United States Patent [19]

Campbell et al.

[11] 4,410,744
[45] Oct. 18, 1983

[54] MAKING 1,2,4-BUTANETRIOL BY HYDROFORMYLATION OF GLYCIDOL

[75] Inventors: Carol J. Campbell, Logan; Jerald C. Hinshaw, Ogden, both of Utah

[73] Assignee: Thiokol Corporation, Chicago, Ill.

[21] Appl. No.: 404,168

[22] Filed: Aug. 2, 1982

[51] Int. Cl.³ .................... C07C 31/22; C07C 29/16
[52] U.S. Cl. .................... 568/864; 260/467; 549/313; 560/186
[58] Field of Search .................... 568/864; 549/313; 560/186

[56] References Cited

U.S. PATENT DOCUMENTS

| | | | |
|---|---|---|---|
| 2,571,967 | 10/1951 | Trenner et al. | 568/864 |
| 2,857,420 | 10/1958 | Hoffman et al. | 568/864 |
| 2,892,844 | 6/1959 | Holmquist | 568/864 |
| 3,008,971 | 11/1961 | Parker et al. | 568/864 |
| 3,770,837 | 11/1973 | Farstritsky et al. | 568/864 |

*Primary Examiner*—J. E. Evans
*Attorney, Agent, or Firm*—Gerald K. White

[57] ABSTRACT

1,2,4-Butanetriol is produced by hydroformylation of a solution of glycidol and reduction of the hydroformylation reaction products.

15 Claims, No Drawings

MAKING 1,2,4-BUTANETRIOL BY HYDROFORMYLATION OF GLYCIDOL

BACKGROUND OF THE INVENTION

Solid rocket propellants contain various plasticizers such as nitroglycerin, 2-hydroxymethyl-1,3-propanediol trinitrate, 2,2-di(hydroxymethyl)-1-propanol trinitrate, and 1,2,4-butanetriol trinitrate. The latter plasticizer is the nitrate ester of 1,2,4-butanetriol. These plasticizers are utilized in propellant formulations to provide energy increase as well as improvements to mechanical properties of the propellant.

1,2,4-butanetriol, the precurser of 1,2,4-butanetriol trinitrate, has been produced by the dehydration of 1,3-butanediol to 3-butene-1-ol, followed by hydroxylation with $H_2O_2$ and a tungsten catalyst in aqueous solution. The compound has also been produced on a laboratory scale by the hydrogenation of malic acid or its esters. In addition, 1,2,4-butanetriol has been produced by the reduction of 2-butyne-1,4-diol to 2-butene-1,4-diol, epoxidation to oxiranebismethanol, followed by hydrogenation over a nickel catalyst. The procedure of this invention is believed to be advantageous, especially with respect to cost considerations, when contrasted with such prior techniques for making 1,2,4-butanetriol.

SUMMARY OF THE INVENTION

This invention relates to a method for producing 1,2,4-butanetriol which generally comprises hydroformylating a solution of glycidol (2,3-epoxy-1-propanol) in a suitable solvent under conditions of elevated temperature and elevated pressure sufficient to cause hydroformylation of the glycidol into a reaction product such as 4-hydroxybutyrolactone or a mixture of 4-hydroxybutyrolactone and alkyl-3,4-di-hydroxybutyrate. Hydroformylation, also known as the Oxo process generally involves the addition of carbon monoxide to alkenes or alkene derivitives such as epoxides in the presence of a catalyst to yield aldehydes and ketones, which can be reduced to alcohol. Hydroformylation in accordance with this invention is accomplished under an atmosphere containing CO and $H_2$ and in the presence of a catalyst such as $Co_2(CO)_8$. The reaction product is then reduced to produce 1,2,4-butanetriol. 1,2,4-butanetriol may then be converted to its trinitrate with use of conventional techniques.

DETAILED DESCRIPTION OF THE INVENTION

According to this invention 1,2,4-butanetriol is prepared by hydroformylation of glycidol solutions under controlled conditions. The hydroformylations reaction may be conveniently performed in an autoclave of conventional design and construction.

A combination of elevated temperature and elevated pressure that is sufficient to cause hydroformylation to occur is utilized to convert glycidol into a reaction product. Typical temperature and pressures useful in the practice of the invention are on the order from 100° C. to 150° C. and 800 psi to 2000 psi because of the necessity of forming and regenerating the active catalytic species, a metal carbonyl hydride, and to drive the reaction to completion.

Hydroformylation of glycidol is accomplished under an atmosphere containing CO and $H_2$. CO and $H_2$ are typically present in ratios from 1:1 to 3:5. A $CO:H_2$ of from 1:1 is useful because the concentration of CO is sufficient to effect convenient reaction rates while the $H_2$ concentration is favorable for formation and recycling of the carbonyl metal hydride, the active catalytic species.

A catalyst is also used to aid hydroformylation of glycidol. Useful catalysts include $Co_2(CO)_8$, $Rh_4(CO)_{12}$, $RhH(CO)(PPh_3)_3$, and other transition metal carbonyl compounds. The amount of catalyst to be added is an amount sufficient to accelerate the hydroformylation reaction. Typically, the glycidol to catalyst molar ratio is from 8:1 to 12:1.

Glycidol solutions for use in the invention are prepared by dissolving the glycidol in an amount of solvent at least sufficient to dissolve all of the glycidol. Typical glycidol concentrations are 0.1 to 2.5 molar. Normally an excess of solvent over that required to place all of the glycidol in solution is utilized because of convenience of handling and working up the reaction mixture. Solvents useful in the practice of the invention include nonparticipating solvents including but not limited to acetone or toluene and participating solvents including but not limited to water and alcohols such as methanol and ethanol. Should a non-participating solvent such as acetone or toluene be utilized, the reaction product comprises 4-hydroxybutyrolactone. Should a participating solvent such as methanol be utilized, the reaction product comprises a mixture of alkyl-3, 4-dihydroxybutyrate and 4-hydroxybutyrolactone. With alcohol the reaction product comprises a mixture of the corresponding ester derived from the alcohol solvent and 4-hydroxybutyrolactone. For example, when methanol is used as the solvent, a reaction product comprising methyl-3,4-dihydroxybutyrate and 4-hydroxybutyrolactone is obtained.

The hydroformylation reaction using acetone as a solvent may be expressed according to the following formula:

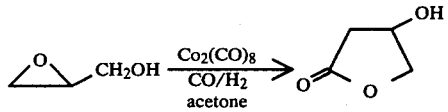

The hydroformylation reaction using methanol as a solvent may be expressed according to the following formula:

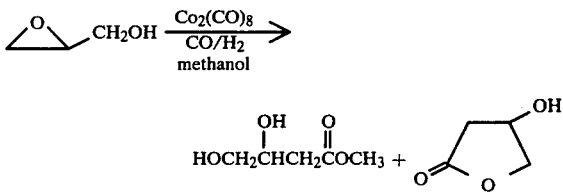

Following hydroformylation, the reaction product, for example, 4-hydroxybutyrolactone, may be separated from other constituents remaining in the autoclave such as the cobalt carbonyl catalyst by addition of acetic acid to form cobalt acetate which may then be removed by filtration. The remaining products may be purified by distillation in vacuuo. The reaction product is then reduced to form 1,2,4-butanetriol. Such reduction may be accomplished by hydrogenation over a hydrogenation catalyst such as a copper chromite or the like.

Alternatively, the reduction may be accomplished with use of a sufficient amount of hydride reducing agent to convert the reaction product to 1,2,4-butanetriol. Typical reducing agents include lithium aluminum hydride, sodium bis(2-methoxyethoxy) aluminum hydride, lithium borohydride, borane, sodium in alcohol, aluminum hydride, alkoxy lithium aluminum hydrides, or sodium borohydride in the presence of ethanedithiol or lithium chloride or aluminum chloride or boron trifluoride.

1,2,4-butanetriol trinitrate may be prepared by treating the above obtained 1,2,4-butanetriol with excess nitric acid, in the presence of a water absorber, such as fuming sulfuric acid, at below normal ambient temperature, 10°–15° C., in the presence of an immiscible solvent, such as methylene chloride, while monitoring the redox potential of the system, while stirring. The immiscible solvent serves the purpose of removing the nitrate ester from the acid phase as it is formed. Combination of reactants is accomplished by incremental addition of the alcohol to the acid. Separation of the phases, if the treatment has been performed in a two phase system, or the addition of a suitable immiscible solvent followed by separation of the organic phase permits recovery of the desired trinitrate from the organic phase by standard techniques. If desired, recovery may be accomplished by neutralization of any acidity present in the organic phase, drying and evaporation of the solvent.

The invention is further illustrated by the following Examples.

EXAMPLE 1

A solution of glycidol (10 ml, 0.15 mole) and $Co_2(CO)_8$ catalyst (2.0 g, 5.8 m mole) in 100 ml of acetone is placed in a stainless steel, stirred autoclave. The vessel is pressurized to 1400 psi with 1:1 $CO:H_2$ and heated to 150° C. with stirring for 4 hours. The reaction is cooled to room temperature and 20 ml of acetic acid is added. After standing overnight the solvent and excess acetic acid are removed under reduced pressure. Acetone (50 ml) is added to the residue and the resulting cobalt acetate precipitate is removed by filtration. The filtrate is concentrated under reduced pressure. The remaining residue is distilled in vacuuo giving 8.0 g. (52%) 4-hydroxybutyrolactone, b.p. 110°–120°@ 0.1 torr. To a stirred slurry of 2.3 g lithium aluminum hydride in 20 ml of dry tetrahydrofuran under $N_2$ cooled in an ice bath is added dropwise a solution of 5 g (0.05 mole) 4-hydroxybutyrolactone in 30 ml dry tetrahydrofuran. After the addition the reaction is stirred and refluxed under $N_2$ for 1 hour. The cooled reaction is carefully hydrolyzed with water and filtered. The filtrate is concentrated under reduced pressure and the remaining oil is distilled in vacuuo giving 1,2,4-butanetriol, 1.0 g (19%), b.p. 150°–165° @ 1 torr, of approximately 90% purity as judged by NMR spectroscopy.

EXAMPLE 2

A reaction similar to that of Example 1 is performed using methanol in place of acetone as the solvent. The reaction product of the hydroformylation reaction is a mixture of methyl-3,4-dihydroxybutyrate and 4-hydroxybutyrolactone. A solution of glycidol (2 ml, 0.03 mole) and $Co_2(CO)_8$ catalyst (0.62 g, 1.80 m mole) in 100 ml of methanol is placed in a stainless steel, stirred autoclave. The vessel is pressurized to 950 psi with 1:1 $CO:H_2$ and heated to 115° C. with stirring for 1.5 hours. The reaction is cooled to room temperature and 20 ml of acetic acid is added. After standing overnight the solvent and excess acetic acid are removed under reduced pressure. Acetone (50 ml) is added to the residue and the resulting cobalt acetate precipitate is removed by filtration. The filtrate is concentrated under reduced pressure. The products are analyzed by gas chromatography/mass spectroscopy in the chemical ionization mode.

We claim:

1. A method for producing 1,2,4-butanetriol, comprising:
   hydroformylating a solution of glycidol in a solvent under conditions of elevated temperature and elevated pressure sufficient to cause hydroformylation of said glycidol under an atmosphere containing CO and $H_2$, and in the presence of a catalyst to produce a reaction product; and reducing said reaction product to produce 1,2,4-butanetriol.

2. The method of claim 1, wherein:
   said solvent is non-participating in the hydroformylation reaction and is a member selected from the group consisting of acetone and toluene and said reaction product comprises 4-hydroxybutyrolactone.

3. The method of claim 1, wherein:
   said solvent is participating in the hydroformylation reaction and is an alcohol and said reaction product comprises a mixture of alkyl-3,4-dihydroxybutyrate and 4-hydroxybutyrolactone.

4. The method of claim 2, wherein:
   said solvent comprises acetone.

5. The method of claim 4, wherein:
   said solvent comprises methanol and said reaction product comprises a mixture of methyl-3,4-dihydroxybutyrate and 4-hydroxybutyrolactone.

6. The method of claim 1, wherein:
   said temperature is from about 100° C. to 150° C.

7. The method of claim 1 or 6, wherein:
   said pressure is from about 800 psi to 2000 psi.

8. The method of claim 1, wherein:
   said CO and $H_2$ are present in a ratio from 1:1 to 3:5.

9. The method of claim 1, wherein:
   said catalyst is selected from the group consisting of $Co_2(CO)_8$, $Rh_4(CO)_{12}$, and $RhH(CO)(PPh_3)_3$.

10. The method of claim 1, wherein:
    said reaction product is reduced by hydrogenation in the presence of a hydrogenation catalyst.

11. The method of claim 10, wherein:
    said hydrogenation catalyst is a copper chromite type.

12. The method of claim 1, wherein:
    said reaction product is reduced by reaction with a hydride reducing agent.

13. The method of claim 12, wherein:
    said hydride reducing agent comprises lithium aluminum hydride.

14. A method for producing 1,2,4-butanetriol, comprising:
    hydroformylating a solution of glycidol in acetone under conditions of a temperature from 100° C. to 150° C., a pressure from 800 psi to 2000 psi, under an atmosphere containing a ratio of 1:1 to 3:5 of $CO:H_2$, and in the presence of a $Co_2(CO)_8$ catalyst to produce 4-hydroxybutyrolactone; and reducing said 4-hydroxybutyrolactone with lithium aluminum hydride to produce 1,2,4-butanetriol.

15. A method for producing 1,2,4-butanetriol, comprising:
    hydroformylating a solution of glycidol in methanol under conditions of a temperature from 100° C. to 150° C., a pressure from 800 psi to 2000 psi, under an atmosphere containing a ratio of 1:1 to 3:5 of $CO:H_2$, and in the presence of a $Co_2(CO)_8$ catalyst to produce a mixture of methyl-3,4-dihydroxybutyrate and 4-hydroxybutyrolactone and reducing said mixture with lithium aluminum hydride to produce 1,2,4-butanetriol.

* * * * *